(12) United States Patent
Rolling

(10) Patent No.: US 7,105,173 B1
(45) Date of Patent: Sep. 12, 2006

(54) NICOTINE REPLACEMENT APPLIQUE

(76) Inventor: Kenneth J. Rolling, 24091 County Road 50, Cold Spring, MN (US) 56320

(*) Notice: Subject to any disclaimer, the term of this patent is extended or adjusted under 35 U.S.C. 154(b) by 592 days.

(21) Appl. No.: 10/104,781

(22) Filed: Mar. 21, 2002

(51) Int. Cl.
*A61K 6/00* (2006.01)
*A61K 7/00* (2006.01)
*A61K 9/00* (2006.01)
*A24F 5/00* (2006.01)

(52) U.S. Cl. .............. 424/400; 424/401; 131/221; 131/424

(58) Field of Classification Search ........ 131/270; 424/64
See application file for complete search history.

(56) References Cited

U.S. PATENT DOCUMENTS

| | | | |
|---|---|---|---|
| 4,762,715 A | 8/1988 | Lukas et al. | |
| 4,774,971 A | 10/1988 | Vieten | |
| 5,035,252 A | 7/1991 | Mondre | |
| 5,048,544 A | 9/1991 | Mascarelli et al. | |
| 5,139,790 A | 8/1992 | Snipes | |
| 5,158,772 A | * 10/1992 | Davis | 424/401 |
| 5,244,668 A | 9/1993 | Snipes | |
| 5,293,883 A | 3/1994 | Edwards | |
| 5,298,257 A | 3/1994 | Bannon et al. | |
| 5,331,979 A | 7/1994 | Henley | |
| 5,540,934 A | 7/1996 | Touitou | |
| 5,580,851 A | 12/1996 | Trinh et al. | |
| 5,593,684 A | * 1/1997 | Baker et al. | 424/435 |
| 5,599,554 A | 2/1997 | Majeti | |
| 5,716,638 A | 2/1998 | Touitou | |
| 5,783,207 A | 7/1998 | Stanley et al. | |
| 5,783,211 A | 7/1998 | Manzo et al. | |
| 5,799,663 A | 9/1998 | Gross et al. | |
| 5,876,758 A | 3/1999 | Meybeck et al. | |
| 6,045,823 A | 4/2000 | Vollhardt et al. | |
| 6,103,247 A | 8/2000 | Boussouira et al. | |
| 6,153,204 A | 11/2000 | Fanger et al. | |

OTHER PUBLICATIONS

Fairclough, Gordon, "Some Pharmacies Sell New Nic-Fix—Lollipops Laced With Nicotine", The Wall Street Journal, Apr. 3, 2002, B1 & B2 pages.

Untitled Article from the Associated Press, Tucker, GA, Apr. 11, 2002, 2 pages.

* cited by examiner

*Primary Examiner*—Carlos A. Azpuru
(74) *Attorney, Agent, or Firm*—Albert W. Watkins

(57) ABSTRACT

Nicotine in base or salt form combined with cosmetic ingredients to form a lip balm or similar stick. The stick is readily dispensed not only onto a person's lips but also may be used on the skin, for example on the wrist. Packaging the nicotine this way enables a smoker to obtain nicotine discretely anywhere in public, without offending others by smoking. Furthermore, the dosage is readily controlled, and the person's hands and mouth are active, similar to the lighting and smoking of a cigarette.

10 Claims, 1 Drawing Sheet

NICOTINE REPLACEMENT APPLIQUE

BACKGROUND OF THE INVENTION

1. Field of the Invention

This invention pertains generally to the field of smoking cessation, and more particularly to a nicotine delivery vehicle which is discrete and self-administered.

2. Description of the Related Art

Persons are, by their very nature, generally curious and explorative. This inherent behavior is one of the characteristics that has been generally beneficial to mankind in comparison to other creatures. However, there are times when this curiosity comes with undesired consequences. One of those times is the experimenting with or usage of tobacco.

While there are a number of short term physical benefits that have been associated with tobacco usage, leading to short-term pleasure, over time man has learned that the longer term usage of tobacco leads to a propensity for a number of physical ailments. These ailments range from serious chronic disorders such as emphysema to acute and life-threatening cancers to greater frequencies of common colds. Depending upon mode of tobacco usage, there are other undesirable consequences beyond the health and well-being of the individual. For example, a burning cigarette may burn small holes in fabric, garments, furniture and the like, and is also occasionally the source of combustion that leads to the destruction of houses and property.

Consequently, many persons who smoke or otherwise consume tobacco products eventually wish to cease such consumption. Unfortunately, this proves to be a far greater challenge than most persons expect or believe. There are a number of very adverse side-effects that are associated with the cessation of tobacco consumption, most which are believed to be a result of nicotine addiction. Nicotine, one of the biologically significant components of tobacco, is powerfully addictive.

In an effort to assist individuals who desire to cease tobacco consumption, a large number of products have been developed which deliver nicotine in controlled amounts to the individual. Nicotine is readily absorbed through a number of the body's membranes and coverings, including the skin, lips and mucous membranes, leading to the implementation of nicotine patches and gums, for example. Transdermal or transmucosal nicotine as a part of smoking cessation is well-documented, for example, in U.S. Pat. Nos. 5,139,790 and 5,244,668 to Snipes; 5,298,257 to Bannon et al; 5,593,684 to Baker et al; 5,599,554 to Majeti; and 5,783,207 to Stanley et al, the teachings of each which are incorporated herein by reference.

When the addictive properties of nicotine were identified, there was an expectation that nicotine replacement through channels other than tobacco would alleviate the challenge smokers and other tobacco consumers had when attempting to discontinue consumption. However, the full extent of the benefit was not realized. Researchers have proposed that tobacco addiction is more complex than a chemical addiction, and that other physical addictions are present, such as the tactile feedback and the kinetics of grasping, lighting and smoking cigarettes. These tactile and kinetic factors play a role in the probability of a person successfully ceasing. Said another way, fidgety hands are one of the well-known problems for an individual trying to "kick the habit."

In this vein, cigarette simulators, or so-called smokeless cigarettes, have been created and are illustrated by Vieten in U.S. Pat. No. 4,774,971; Edwards in 5,293,883; Henley in 5,331,979; and Gross et al in 5,799,663. These patents illustrate controlled nicotine dosage in combination with the presentation of nicotine through a mouthpiece resembling a cigarette. However, cigarette smoking has lost favor among many people, and the mere presence of a cigarette, smokeless or otherwise, is undesirable. For exemplary purposes only, one such instance would be in a non-smoking section of a restaurant. While the cigarette simulators produce no smoke, their presence might be mistaken for an actual cigarette, leading to a potentially undesirable disturbance.

Two less relevant patents, 5,035,252 to Mondre and 5,048,544 to Mascarelli et al, show unusual alternative nicotine treatments that are merely representative of a large area of research and development. Nevertheless, these prior art approaches signify the extent of development in this large and important industry, and the continuing, unmet need for better tools and techniques pertaining to smoking cessation.

SUMMARY OF THE INVENTION

The present invention combines nicotine in base or salt form with cosmetic ingredients to form a lip balm, lipstick or similar stick. The stick is readily dispensed not only onto a person's lips but also may be used on the skin, for example by smearing on the wrist, ankle or elsewhere. Packaging the nicotine into standard cosmetic products enables a tobacco user to obtain nicotine discretely, in public, and without offending others. In many instances, persons unfamiliar with the product will not even know or recognize the consumption of nicotine. Dosage is readily controlled by the extent of application, which enables the person to adjust according to short-term fluctuations in desire or need for nicotine. Through the process of application, using cosmetic sticks which resemble cigarettes in size and shape, the person's hands are active, similar to the lighting and smoking of a cigarette or cigar. In the case of a lip balm or lipstick, the activity and motion which generate tactile and kinetic feedback closely resemble smoking.

In a first manifestation, the invention is a method for smoking cessation, characterized by a person self-administering nicotine. Nicotine is combined with cosmetic ingredients to form a topical assuagement. This assuagement is then packaged in a cosmetic dispenser stick and delivered to at least one person. The person self-administers the topical assuagement, and obtains beneficial tactile-kinetic feedback resultant to the self-administration.

In a second manifestation, the invention is a stick cosmetics dispenser that offers discrete usage, controlled dosage, and activity for a person's hands during application, combined with a nicotine-containing composition comprising nicotine and a carrier which is solid at room temperature and contact-transferable to a person's body.

In a third manifestation, the invention is a lipstick. A lipstick dispenser stick is provided for containing and dispensing a lipstick composition. The lipstick composition contains nicotine and a carrier.

OBJECTS OF THE INVENTION

A first object of the invention is to provide a smoking cessation product which is visually indistinguishable from standard commercial cosmetics. A second object of the invention is to provide a smoking cessation product which is readily carried by a person, and which may be used frequently, or as desired, without adverse cosmetic effect.

Another object of the present invention is to provide a user-administered dosage of nicotine, which is available for real-time dosage adjustment according to the individual's needs and desires. A further object of the invention is to produce a product which can be readily inventoried by a retailer. Yet another object of the present invention is to enable the self-administration of nicotine through diverse applicators, further expanding the discrete nature of the product.

BRIEF DESCRIPTION OF THE DRAWINGS

The foregoing and other objects, advantages, and novel features of the present invention can be understood and appreciated by reference to the following detailed description of the invention, taken in conjunction with the accompanying drawing, which illustrates the preferred manufactured lip balm from a projected view.

DESCRIPTION OF THE PREFERRED EMBODIMENT

Figure 1:
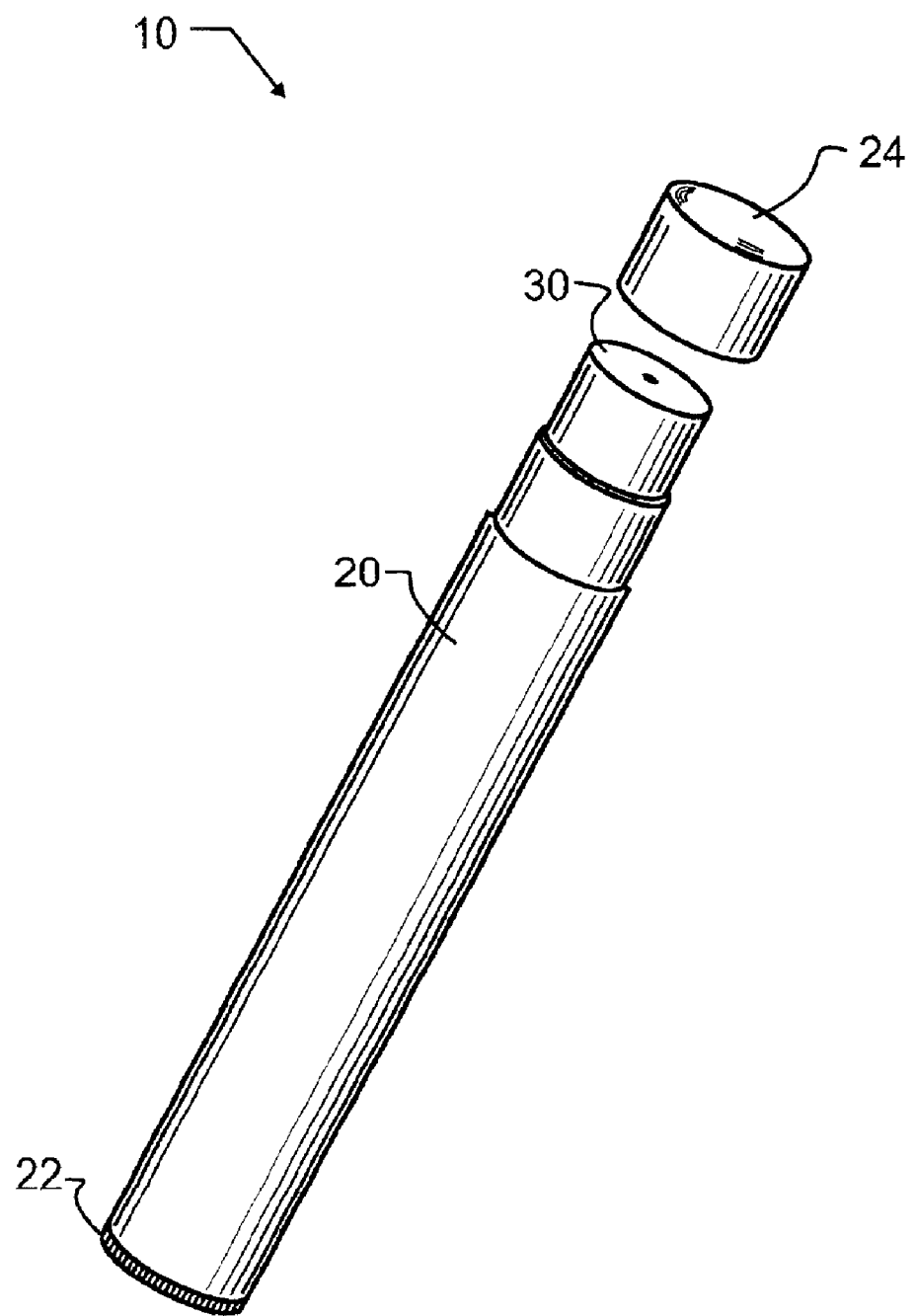

Exemplary embodiments of the present invention solve inadequacies of the prior art by providing cosmetic compositions that are visually indistinguishable from existing cosmetics, but which contain nicotine. The illustrated preferred embodiment lip balm 10 includes a dispenser 20 having a spin extender 22 and removable cover 24. Within dispenser 20 is a stick of lip balm composition 30. Lip balm composition 30 is produced as a chemical cosmetic composition including ingredients known in the art, selected and processed accordingly. Typical ingredients will include a low-melt wax, either as a single wax ingredient or a wax blend. This wax or wax blend is formulated to act as a carrier for the remaining ingredients, and will most preferably be soft but still solid enough to retain shape at or slightly above room temperature. The wax will also most preferably offer adhesion or stick to a warm body or lips of a person, desirably with a thin coating or good spread upon application. For the purposes of the present disclosure, this will be referred to as being contact-transferable. The extent of transfer and quality thereof is dependent upon the waxes chosen, their rheology in combination with the remaining ingredients and other factors too complex for the present disclosure. Nevertheless, these properties and characteristics are known and well documented in the lipstick and lip balm industry. Waxes or blend components, provided for exemplary purposes only and not intended to be limiting, include carnauba wax, montan wax, beeswax, cocoa butter, microcrystalline wax, paraffin, polyethylene and the like. Various natural or synthetic oils, jellies, fatty acids, fats and the like may be used in addition or instead of the aforementioned waxes, including but not limited to petrolatum, vegetable and petroleum oils and jellies, and the like. In most instances, it will be preferable to use a viscous composition as the carrier.

To the carrier a variety of additives are known, depending upon the commercial presentation of features or benefits. For example, emollients such as lanolin, aloe vera or the like may be provided. Various perfumes and scents, flavors, oils, vitamins, herbs, pigments, glossing agents, alcohols and esters, preservatives and the like may also be incorporated. Other ingredients known in the cosmetics industry, some which are very specialized such as micro-encapsulated particles or powders, may additionally be incorporated as desired.

To the foregoing ingredients a small amount of nicotine is added. Nicotine is a heterocyclic compound that exists in both a free base and a salt form. The free base is extremely volatile and is absorbed readily through the mucous membranes and skin. However, the free base tends to decompose in the presence of oxygen, and has a tendency to irritate the mucous membranes. Consequently, while the nicotine may be in simple form, it may somewhat more preferably take the form of a salt of nicotine or other biologically compatible and absorbed form. The exact percentage of nicotine is not critical to the invention, provided there is sufficient nicotine to be bio-affective, and preferably not enough to render the cosmetic composition bio-hazardous or toxic. Standard oral nicotine doses range from about 0.5 to about 4 milligrams, and the $LD_{50}$ oral level is approximately 55 milligrams per Kilogram of body weight, or about 250 mg for a small infant. Consequently, for a preferred lip balm which contains approximately 4 grams total weight, 250 milligrams of nicotine would raise the level to a borderline toxicity level for a small newborn or infant were they to consume the entire stick. This is approximately 6 percent by weight nicotine. Inherent to the wax formulation, the absorption of nicotine is delayed from the oral levels pertaining to acute toxicity, which provides a greater safety margin. This level of 250 milligrams provides ample nicotine for the targeted single application dosage, depending of course upon the amount of balm applied, with an expected range of from 500 light applications, yielding 0.5 milligrams each, to as little as 50 very heavy applications at about 5 grams each. To provide an even greater safety margin, it is preferred to use lower amounts of nicotine, or to limit the amount of cosmetic formulation 30 provided within dispenser 20, such that if a small child or infant were to accidentally ingest the entire stick, there would be a low potential for toxicity. For larger applicators, the weight percentages of nicotine may desirably be reduced to preserve the desired safety margins, or, as aforementioned, limit the total amount of cosmetic formulation 30 to a safe level, irrespective of dispenser 20 size.

The nicotine or nicotine salt will desirably be homogeneously incorporated into the remaining cosmetic formulation. This may be accomplished at the time of blending of the other ingredients, or may be a separate step in the process. The nicotine may be added to a molten wax blend, but may alternatively be introduced through a mechanical blender or homogenizer, or through powdered or frozen powdered ingredients stirred together, provided the carrier will permit one or more of the foregoing.

Once lip balm composition 30 has been formulated, composition 30 will then be shaped and inserted into dispenser 20. Shaping maybe through molten processes or mechanical pressing or other suitable techniques as are known in the industry and as permitted by the actual composition. Lip balm 10 is then ready for distribution.

When a person applies lip balm 10, they may apply it in the same manner as standard lip balm. This ensures that there is little education required of the consumer. However, application of lip balm composition 30 is not limited strictly to one's lips, and the balm may be applied to other parts of one's body. For the purposes of this disclosure, the balm will be referred to as a topical assuagement, since the balm satisfies one's cravings for nicotine, thereby calming or pacifying the individual.

The use of a stick or similar package geometry is preferred, since the stick roughly resembles a cigarette or the like. The retrieval and manipulation of lip balm 10, including application to one's lips, resembles the tactile and kinetic feedback obtained during the retrieval and lighting of a cigarette. This resemblance is far closer than obtained, for example, with a nicotine chewing gum or the like. Consequently, lipstick or lip balm represent the most preferred embodiments of the present invention.

Additional embodiments are also contemplated herein. The field of cosmetics includes a number of other products which are well suited for the introduction of nicotine, in accord with the present invention. Among these are eye liner pencils, cosmetic pencils, cosmetic markers, lip moisturizers, and the like. Depending upon the cosmetic product, the above description regarding the toxicity levels and dosage will need to be adjusted. For example, the amount of applied brow pencil material is minimal, requiring a much higher concentration of nicotine for an effective dosage. This would normally be acceptable, since a pencil of typical design would not be ingested in entirety by an infant. Furthermore, the total amount of material within a brow pencil is normally less, allowing a greater concentration of nicotine without changing the total amount of nicotine present. From the foregoing, it should be apparent that alternative embodiments encompass a number of cosmetic products, particularly those having the preferred stick geometry.

While the foregoing details what is felt to be the preferred embodiment and some of the available alternative embodiments of the invention, no material limitations to the scope of the claimed invention are intended. Further, features and design alternatives that would be obvious to one of ordinary skill in the art are considered to be incorporated herein. The scope of the invention is set forth and particularly described in the claims hereinbelow.

I claim:

1. A method for smoking cessation characterized by a person self-administering nicotine, comprising the steps of:

combining nicotine in a range of about 0.5 to about 5 mg/dose with a lip balm composition comprising wax to form a topical assuagement;

packaging said topical assuagement by the steps of shaping said topical assuagement into a cosmetic stick and inserting said shaped cosmetic stick into a lip stick dispenser encompassing said cosmetic stick and having an open tubular end and means for advancing said cosmetic stick towards said open end; and delivering said packaged topical assuagement to at least one person.

2. The smoking cessation method of claim 1 wherein said the step of self-administering comprises said at least one person applying said topical assuagement to said at least one person's lips.

3. The smoking cessation method of claim 1 wherein said nicotine is selected from the group consisting of nicotine and nicotine salts.

4. The smoking cessation method of claim 1 wherein said topical assuagement consists essentially of nicotine and a low melting point wax.

5. The combination of claim 1 wherein said lip balm composition further comprises a pigment.

6. The combination of claim 1 wherein said viscous carrier consists essentially of a wax having a softening point in the range of 50 to 100 degrees Fahrenheit.

7. The combination of claim 1 wherein said lip balm composition further comprises an emollient.

8. The combination of claim 1 wherein said viscous carrier is solid at room temperature and contact-transferable.

9. The lipstick of claim 1, wherein said topical assuagement comprises approximately 6 percent by weight of said nicotine.

10. The lipstick of claim 1 wherein said topical assuagement has a total nicotine content below the $LD_{50}$ oral level for infants.

* * * * *